United States Patent
Castrodale

(10) Patent No.: US 8,323,206 B2
(45) Date of Patent: Dec. 4, 2012

(54) MOUTHPIECE WITH EJECTION AND ALIGNMENT MECHANISMS

(75) Inventor: Alan C. Castrodale, Littleton, CO (US)

(73) Assignee: Lifeloc Technologies, Wheat Ridge, CO (US)

( * ) Notice: Subject to any disclaimer, the term of this patent is extended or adjusted under 35 U.S.C. 154(b) by 1263 days.

(21) Appl. No.: 12/056,528

(22) Filed: Mar. 27, 2008

(65) Prior Publication Data

US 2009/0247892 A1    Oct. 1, 2009

(51) Int. Cl.
*A61B 5/08* (2006.01)
*A61B 17/42* (2006.01)

(52) U.S. Cl. .......... 600/529; 600/35; 600/530; 600/532; 600/538; 436/132

(58) Field of Classification Search .......... 600/529, 600/530, 532, 538, 35; 436/132; 435/2
See application file for complete search history.

(56) References Cited

U.S. PATENT DOCUMENTS

| | | | | |
|---|---|---|---|---|
| 3,817,158 A | * | 6/1974 | Reinbeck et al. | 493/39 |
| 4,740,475 A | * | 4/1988 | Paul | 436/165 |
| 5,291,898 A | * | 3/1994 | Wolf | 600/532 |
| 6,008,276 A | * | 12/1999 | Kalbe et al. | 524/47 |
| 7,171,842 B2 | * | 2/2007 | Stock et al. | 73/23.3 |
| 7,364,551 B2 | * | 4/2008 | Allen et al. | 600/529 |
| D606,434 S | * | 12/2009 | Castrodale et al. | D10/81 |
| 2004/0050718 A1 | * | 3/2004 | Traylor, III | 205/787 |
| 2004/0260194 A1 | * | 12/2004 | Bayer et al. | 600/529 |
| 2007/0016092 A1 | * | 1/2007 | Shaw et al. | 600/532 |
| 2007/0093725 A1 | * | 4/2007 | Shaw | 600/543 |
| 2010/0063408 A1 | * | 3/2010 | Nothacker et al. | 600/532 |
| 2010/0204600 A1 | * | 8/2010 | Crucilla | 600/532 |

* cited by examiner

*Primary Examiner* — Ethan Whisenant
(74) *Attorney, Agent, or Firm* — HolzerIPLaw, PC

(57) ABSTRACT

A mouthpiece with an eject mechanism is disclosed. The mouthpiece includes an eject mechanism adapted to conform to a testing device, such as a breath analysis device. The eject mechanism allows for hygienic removal of a used mouthpiece from the testing device. A guiding surface allows for alignment of the mouthpiece with the testing device.

20 Claims, 3 Drawing Sheets

MOUTHPIECE WITH EJECTION AND ALIGNMENT MECHANISMS

BACKGROUND

Breath analysis devices are commonly used as medical diagnostic tools. The chemicals present in a subject's breath can provide a wealth of information regarding the health and physical condition of a person. For example, non-invasive, breath analysis tests have been developed to detect lung cancer and breast cancer, lactose intolerance, kidney malfunction, liver malfunction, asthma, diabetes, ulcers, schizophrenia, neurological disorders, pneumonia, halitosis, and organ trauma among other medical conditions. Breath analysis is also commonly used to determine blood alcohol content.

Breath analysis generally requires that the subject's mouth be in contact with the testing device or apparatus. Single-use, disposable mouthpieces, often constructed of plastics such as polyethylene, are often used with breath analysis devices. The disposable mouthpieces are used for sanitary and health considerations. When a subject blows into a mouthpiece, solid or liquid debris, saliva, blood, or other substances that are in the mouth of the subject often pass into the mouthpiece through the inlet port and may exit the mouthpiece through the exhaust port. Thus, it is undesirable and unsanitary for the subject or the person administering the test to contact the mouthpiece while removing the mouthpiece from the breath analysis device.

The information included in this Background section of the specification, including any references cited herein and any description or discussion thereof, is included for technical reference purposes only and is not to be regarded as subject matter by which the scope or field of the invention is to be bound.

SUMMARY

Implementations described and claimed herein address the foregoing and other situations by providing a mouthpiece for breath analysis that allows for ejection of the mouthpiece from the breath analysis device without requiring contact with portions of the mouthpiece that may have been in contact with a subject's bodily fluids or debris from a subject's mouth. Because the ejection mechanism is a part of the mouthpiece, ejection functionality may be added to existing test devices at a minimal cost.

In one implementation, a mouthpiece comprising an eject mechanism adapted to conform to a testing device, such as a breath analysis device or breathalyzer, is provided. In one implementation, the ejection mechanism may be a lever. In some aspects, a first portion of the eject mechanism extends perpendicularly from a port in the mouthpiece along the side of the testing device and may aid in aligning the mouthpiece with the testing device. A second portion of the eject mechanism may extend perpendicularly from the first portion of the eject mechanism. In other aspects, this second portion of the eject mechanism may be textured to provide traction. The mouthpiece may be adapted to attach to the testing device by frictional attachment, or in another detachable manner. In yet other aspects, the ejection mechanism is formed continuously with the mouthpiece. In still other aspects, the ejection mechanism extends from a port in the mouthpiece without impinging airflow through the mouthpiece or obstructing access to any port in the mouthpiece. The mouthpiece may comprise polyethylene, polypropylene, EverCorn™, BIOPAR®, Plantic® thermoplastic starch polymer, or other plastic, metal, or a mixture or combination thereof.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the claimed subject matter will be apparent from the following more particular written Detailed Description of various implementations and implementations as further illustrated in the accompanying drawings and defined in the appended claims.

BRIEF DESCRIPTION OF THE DRAWINGS

Implementations of the invention may be understood from the following Detailed Description describing various implementations read in connection with the accompanying drawings.

DETAILED DESCRIPTION

Figure 1:
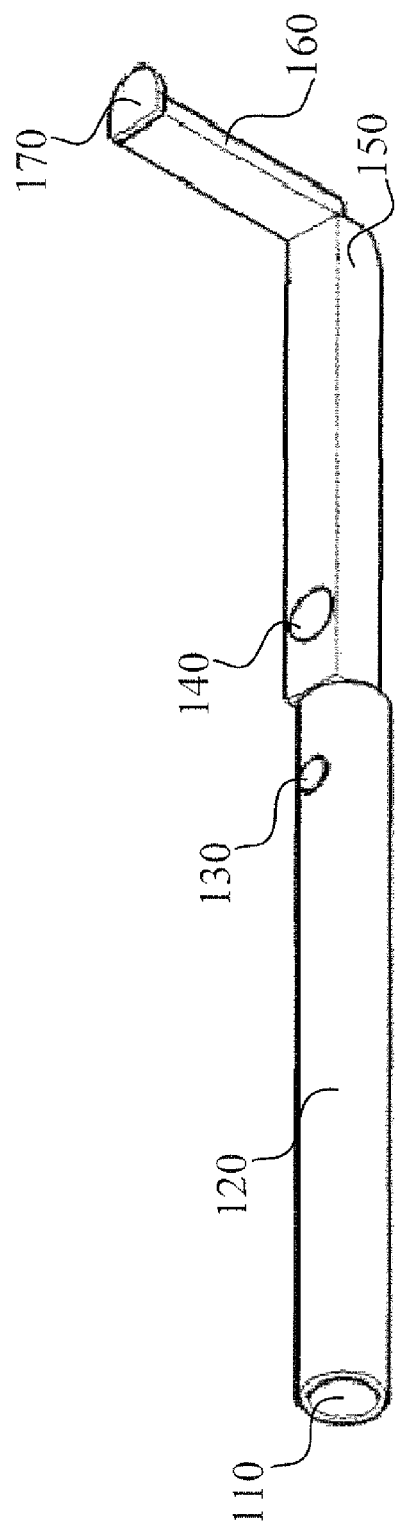
FIG. 1 is a view of a mouthpiece having an eject mechanism.

Referring now to the drawings, FIG. 1 shows a mouthpiece having an eject mechanism. FIG. 1 shows a hollow mouthpiece 100 having an inlet port 110 at a proximal end of the mouthpiece 100 and an exhaust port 150 at a distal end of the mouthpiece 100. The inlet portion 110 allows for a subject to breathe into the mouthpiece 100. Upon exhalation, the subject's breath travels through a tubular portion 120 of the mouthpiece 100 and exits through the exhaust port 150. A pressure sensing port 130 allows for a testing apparatus to sense the pressure of breath as it passes through the mouthpiece 100. A breath sampling port 140 allows for breath to be sampled by the testing device as it passes through the mouthpiece 100. The breath sampling port 140 may also allow for frictional attachment of the mouthpiece to the testing device. A lever 160 extends at an angle from the distal end of the mouthpiece 100. In an implementation, the lever 160 extends perpendicularly from the mouthpiece 120. An ejection surface 170 is provided at an angle (e.g., perpendicular) to the lever 160. In an implementation, the lever 160 and/or the ejection surface 170 may be depressed by the finger of a user to dislodge or eject the mouthpiece 100 from a breath analysis device.

In the implementation of FIG. 1, the ejection mechanism extends away from the portion of the mouthpiece 120 that contacts a subject undergoing testing. Because the portion of the mouthpiece 120 contacts the subject and may come into contact with any substance in the subject's mouth, the portion of the mouthpiece 120 typically comprises a biocompatible, nonreactive materials such as polyethylene, polypropylene, EverCorn™, BIOPAR®, Plantic® thermoplastic starch polymer, or other plastics or biodegradable materials, metals, or a mixture or combination thereof. The ejection mechanism may comprise the same material and be formed integrally with the portion of the mouthpiece 120 that contacts the subject. However, the ejection mechanism may also be formed of another material, such as a metal or another polymer, or be attached with the mouthpiece 100. While the implementation shown in FIG. 1 includes an ejection surface 170, which may be textured to provide traction, the end of lever 160 that does not contact the portion of the mouthpiece 120 may also be used to eject the mouthpiece 100 from the testing device.

The mouthpiece 100 may be constructed in any size or shape suitable for use with the desired test device. For example, the sizes and shapes of the inlet port 110 and the exhaust port 150 may vary according to the test device. The pressure sensing port 130 may be placed at any location along the mouthpiece suitable for sensing the pressure of the subject's breath as it flows from the inlet port 110 to the exhaust port 150. The breath sampling port may be placed at any location along the mouthpiece suitable for sampling the subject's breath as it flows from the inlet port 110 to the exhaust port 150. The location and size of the breath sampling port 140 may also vary in accordance with the way in which the mouthpiece 100 is attached to the test device. In an implementation, the mouthpiece may be attached to the test device using an external adhesive or fixative. In another implementation, the lever 160 may be of any length suitable to remove a user's hands from debris or fluids that may enter the mouthpiece 100.

Figure 2:
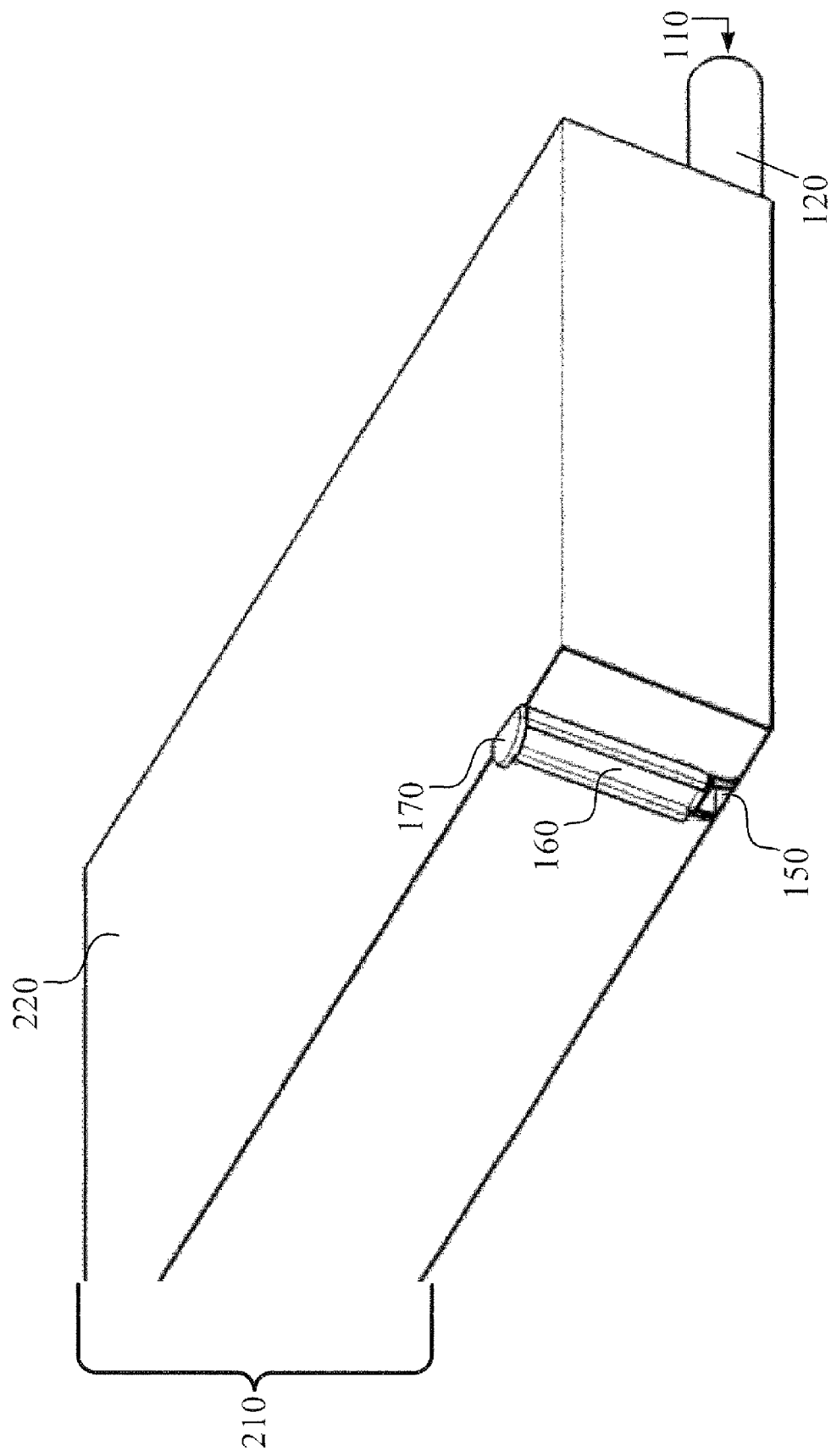
FIG. 2 is a view of the mouthpiece of FIG. 1 affixed to a testing device.

FIG. 2 is a view 200 of the mouthpiece 100 mated with a test device 210, such as a breath analysis device. As illustrated in FIG. 2, breath analysis device 210 includes a display surface 220 and a recess on the bottom portion of the device adapted to receive the mouthpiece 100. The inlet port 110 extends away from the test device 210, so that the subject has unobstructed access to the inlet port during the sampling portion of the breath analysis process. The mouthpiece 100 is frictionally attached to the test device at attachment port 140 (not shown). The exhaust port 150 is flush with edge of the test device 210, but may also extend beyond the test device. The lever 160 extends at an angle (e.g., perpendicularly) from the portion of the mouthpiece 120 along the edge of the test device 210. The lever 160 may be of any length. The ejection surface 170, which may be textured, extends at an angle (e.g., perpendicularly) from the lever 160 and may be of any size suitable for applying pressure with one or more fingers of a user. In an implementation, the lever 160 and/or the ejection surface 170 may be depressed by the finger of a user to dislodge or eject the mouthpiece 100 from a breath analysis device.

The lever 160 and the ejection surface 170 are oriented so that they remain above the inlet port 110 and the exhaust port 150. Thus, any saliva, food particles, vomitus, or any other debris that passes through or toward the inlet port 110 or the exhaust port 150 will fall away from the lever 160 and the ejection surface 170. As a result, the lever 160 and the ejection surface 170 remain sanitary throughout the breath analysis process, without the need for additional sanitary measures such as the use of latex gloves. While FIG. 2 illustrates the ejection mechanism extending from the exhaust port, the ejection mechanism may be adapted to extend along the test device from any portion of the mouthpiece.

In the implementation of FIG. 2, the ejection surface 170 is parallel to and extends away from the display surface 220. Thus, the ejection surface facilitates the ejection of the mouthpiece by operator of the test device or the subject without impeding access to the inlet port 110 or the exhaust port 150 at any point during the testing process. Ejection of the mouthpiece requires only a slight movement of one of the operator's fingers from the display surface. However, the ejection surface need not be placed in the same plane as the display surface 220. The ejection surface may extend from any point on the lever and be of any size. Further, because the ejection mechanism is incorporated into the mouthpiece, ejection functionality may be added to existing test devices at a minimal cost.

Note that lever 160 in FIG. 2 is constructed in a square channel configuration in order to provide additional support for the lever arm. Other configurations, such as an I-beam, L-beam, T-beam, tapered channel, ribbing, or the like may be used to enhance the rigidity of the lever portion. Alternatively, a more rigid material may be used to construct the lever portion of the eject mechanism. The lever may be constructed of any length sufficient to remove the end of the lever and/or the ejection surface from the inlet and exhaust ports.

Figure 3:
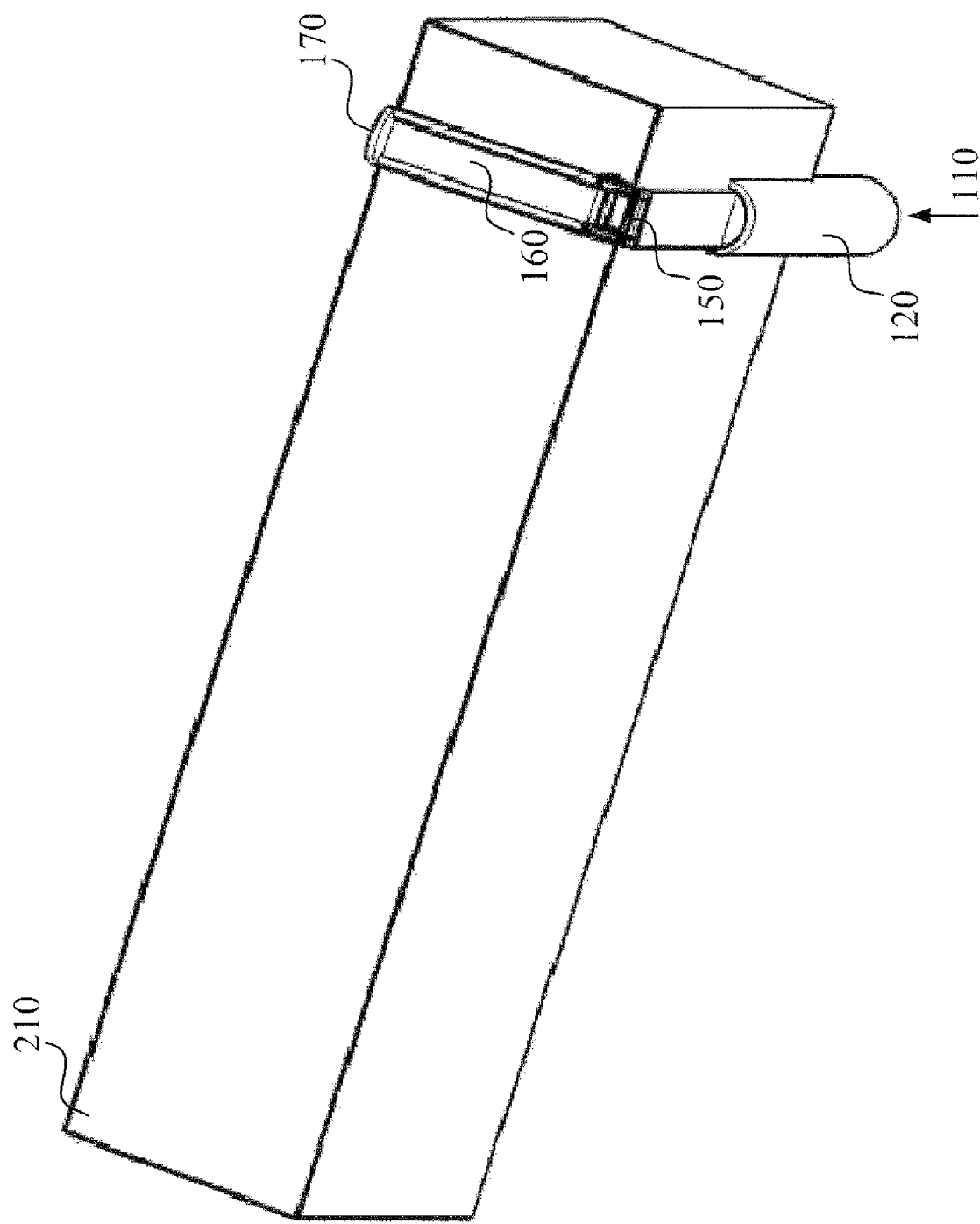
FIG. 3 is another view of the mouthpiece and testing device shown in FIG. 2.

FIG. 3 is another view 300 of the mouthpiece and testing device of FIG. 2 including a recess (not shown) for receiving the mouthpiece 100. More specifically, FIG. 3 illustrates the mouthpiece 100 installed on testing device 210 that is adapted to receive the mouthpiece 100. The inlet portion 110 extends from the testing device unobstructed. The portion of the mouthpiece 120 that contacts the subject fits within the recess in the test device 210 so that the exhaust port 150 is at least partially contained within the recess. The lever 160 extends upward and away from the exhaust port and follows the edge of the testing device. The ejection surface 170 extends perpendicularly from the lever 160.

As can be seen in FIG. 3, the recess may aid in alignment of the mouthpiece when the operator installs the mouthpiece on the test device. Because lever 160 is adapted to conform to the test device, lever 160 may provide a guiding surface that assists in alignment of the mouthpiece with the testing device 210 by, for example, mechanically stopping the mouthpiece from moving beyond the correct operating position of the mouthpiece. If the operator attempts to move the mouthpiece beyond the appropriate operating position, the guiding surface will prevent further movement of the mouthpiece. Thus, the lever 160 may provide for easier installation of the mouthpiece on the test device by providing a surface that guides the mouthpiece into position on the test device when, for example, visibility is limited or when the operator is distracted.

While FIG. 3 illustrates a recess in the test device adapted to receive the mouthpiece, the mouthpiece need not be recessed in the test device. The size and shape of the inlet and exhaust ports, the sample port, the attachment port, the lever, and the length of the mouthpiece may be adapted to suit any test device.

The above specification, examples and data provide a complete description of the structure and use of a mouthpiece with an ejection mechanism. Although various implementations of mouthpieces with ejection mechanisms have been described above with a certain degree of particularity, or with reference to one or more individual implementations, those skilled in the art could make numerous alterations to the disclosed implementations without departing from the spirit or scope of this invention. It is intended that all matter contained in the above description and shown in the accompanying drawings shall be interpreted as illustrative only of particular implementations and not limiting. Changes in detail or structure may be made without departing from the basic elements of the invention as defined in the following claims.

I claim:

1. A mouthpiece, comprising:
   an ejection mechanism adapted to conform to a testing device, wherein a first portion of the ejection mechanism extends perpendicularly from the mouthpiece along the side of the testing device to provide a lever.

2. A mouthpiece according to claim 1, wherein a second portion of the ejection mechanism extends perpendicularly from the first portion of the ejection mechanism.

3. A mouthpiece according to claim 2, wherein a surface of the second portion of the ejection mechanism is textured to provide fraction.

4. A mouthpiece according to claim 1, wherein the mouthpiece is adapted to be frictionally attached to the testing device.

5. A mouthpiece according to claim 1, wherein the mouthpiece is detachably attached to the testing device.

6. A mouthpiece according to claim 1, wherein the ejection mechanism is formed continuously with the mouthpiece.

7. A mouthpiece according to claim 1, wherein the ejection mechanism extends from a port in the mouthpiece without impinging airflow through the mouthpiece.

8. A mouthpiece according to claim 1, wherein the length of the ejection mechanism allows unobstructed access to an inlet port and an exhaust port of the mouthpiece.

9. A mouthpiece according to claim 1, wherein the ejection mechanism is a lever.

10. A mouthpiece according to claim 1, wherein the ejection mechanism extends from a port of the mouthpiece and provides a mechanical stop to align the mouthpiece with the test device.

11. A mouthpiece according to claim 1, wherein the mouthpiece is adapted to be mated with the test device.

12. A mouthpiece according to claim 1, wherein the mouthpiece comprises a biodegradable material.

13. A mouthpiece according to claim 1, wherein the mouthpiece comprises a metal.

14. A mouthpiece, comprising:
    a guiding surface to align the mouthpiece with a test device; and
    an ejection mechanism adapted to conform to the test device, wherein a first portion of the ejection mechanism extends perpendicularly from the mouthpiece along the side of the test device to conform with the testing device and provide a lever.

15. A mouthpiece according to claim 14, wherein the guiding surface provides a mechanical stop.

16. A mouthpiece according to claim 14, wherein the mouthpiece comprises a biodegradable material.

17. A method, comprising:
    forming a mouthpiece having a lever adapted to conform to a testing device, wherein the lever operates as an ejection mechanism and extends perpendicularly from the mouthpiece along a side of the testing device.

18. A method according to claim 17, wherein the lever is formed integrally with the mouthpiece.

19. A method according to claim 17, wherein the mouthpiece comprises biodegradable material.

20. A mouthpiece according to claim 14, wherein a second portion of the ejection mechanism extends perpendicularly from the first portion of the ejection mechanism.

\* \* \* \* \*